US008852538B2

(12) United States Patent  
Olbert et al.

(10) Patent No.: US 8,852,538 B2  
(45) Date of Patent: Oct. 7, 2014

(54) REACTOR FOR CARRYING OUT AN AUTOTHERMAL GAS-PHASE DEHYDROGENATION

(75) Inventors: Gerhard Olbert, Dossenheim (DE); Ulrike Wegerle, Worms (DE); Grigorios Kolios, Neustadt (DE); Carlos Tellaeche Herranz, Heidelberg (DE); Reinhold Höchst, Frankenthal (DE); Andrea Gienger, Meckenheim (DE); Roland Bauer, Offstein (DE)

(73) Assignee: BASF SE (DE)

( * ) Notice: Subject to any disclaimer, the term of this patent is extended or adjusted under 35 U.S.C. 154(b) by 213 days.

(21) Appl. No.: 13/564,028

(22) Filed: Aug. 1, 2012

(65) Prior Publication Data

US 2013/0035531 A1 Feb. 7, 2013

Related U.S. Application Data

(60) Provisional application No. 61/514,100, filed on Aug. 2, 2011.

(51) Int. Cl.
*B01J 19/24* (2006.01)
*C07C 5/48* (2006.01)
(Continued)

(52) U.S. Cl.
CPC ...... *B01J 19/2485* (2013.01); *B01J 2219/2422* (2013.01); *C07C 5/48* (2013.01);
(Continued)

(58) Field of Classification Search
CPC .......... B01J 7/00; B01J 19/00; B01J 19/0013; B01J 19/0053; B01J 19/24; B01J 19/2485; B01J 8/00; B01J 8/008; B01J 8/0285; B01J 2219/00006; B01J 2219/0004; B01J 2219/00835; B01J 2219/00873; B01J 2219/2479; B01J 16/005
USPC .................. 422/129, 198, 600, 630, 631, 633
See application file for complete search history.

(56) References Cited

U.S. PATENT DOCUMENTS 5,023,276 A * 6/1991 Yarrington et al. ........... 518/703
5,678,725 A * 10/1997 Yamada et al. .......... 220/592.21
(Continued)

FOREIGN PATENT DOCUMENTS

DE 4026566 A1 2/1992
EP 472009 A1 * 2/1992
EP 1645540 A1 * 4/2006

OTHER PUBLICATIONS

U.S. Appl. No. 13/564,090, filed Aug. 1, 2012, Olbert et al.

*Primary Examiner* — Natasha Young
(74) *Attorney, Agent, or Firm* — Drinker Biddle & Reath LLP

(57) ABSTRACT

A reactor in the form of a cylinder or prism wherein
the interior of the reactor is divided by a cylindrical or prismatic gastight housing G which is arranged in the longitudinal direction of the reactor into
an inner region having one or more catalytically active zones, in which in each case a packing composed of monoliths stacked on top of one another, next to one another and behind one another and before each catalytically active zone in each case a mixing zone having solid internals are provided, and
an outer region B arranged coaxially to the inner region A, wherein the inner region A is insulated from the outer region B of the reactor by means of a microporous high-performance insulation material having a thermal conductivity 1 at temperatures up to 700° C. of less than 0.05 W/m*K is proposed.

12 Claims, 7 Drawing Sheets

(51) Int. Cl.
*B01J 7/00* (2006.01)
*B01J 8/00* (2006.01)
*B01J 8/02* (2006.01)
*B01J 19/00* (2006.01)
*B01J 19/02* (2006.01)
*B01J 16/00* (2006.01)

(52) U.S. Cl.
CPC ... *B01J 2219/2443* (2013.01); *B01J 2219/2411* (2013.01); *B01J 2219/2416* (2013.01); *B01J 2219/00155* (2013.01); *B01J 2219/2419* (2013.01)

USPC ........... 422/631; 422/129; 422/198; 422/600; 422/630; 422/633

(56) References Cited

U.S. PATENT DOCUMENTS

| | | | |
|---|---|---|---|
| 7,034,195 B2 | 4/2006 | Schindler et al. | |
| 7,255,848 B2* | 8/2007 | Deluga et al. | 423/648.1 |
| 7,270,688 B2* | 9/2007 | Childress et al. | 48/61 |
| 7,388,109 B2* | 6/2008 | Machhammer et al. | 562/549 |
| 2007/0175094 A1* | 8/2007 | Reinke et al. | 48/127.9 |
| 2008/0119673 A1 | 5/2008 | Hechler et al. | |

\* cited by examiner

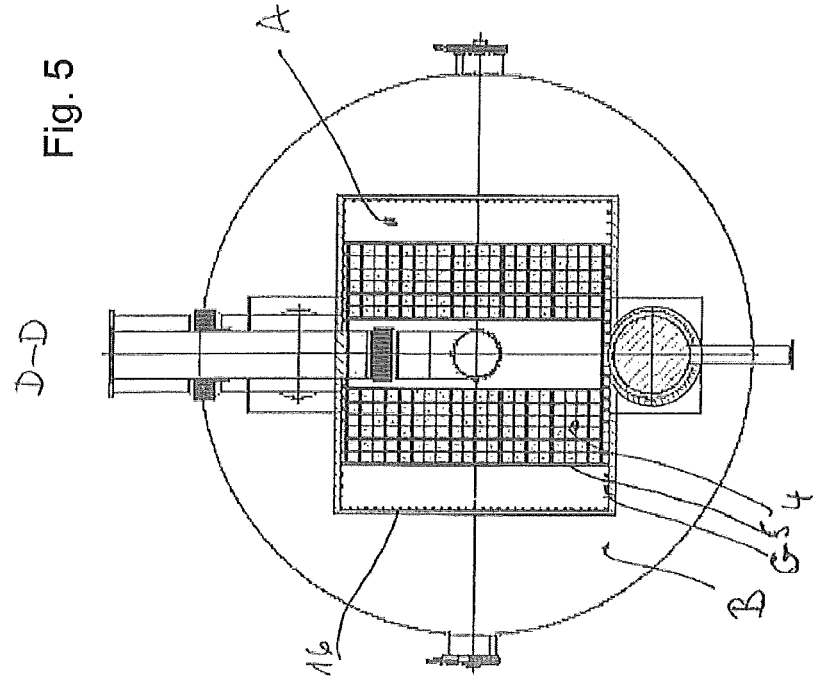
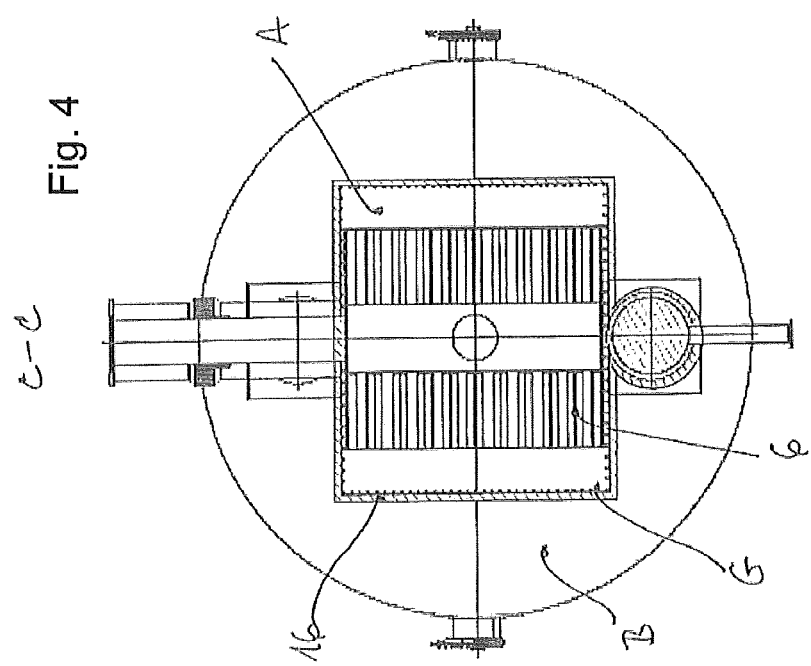

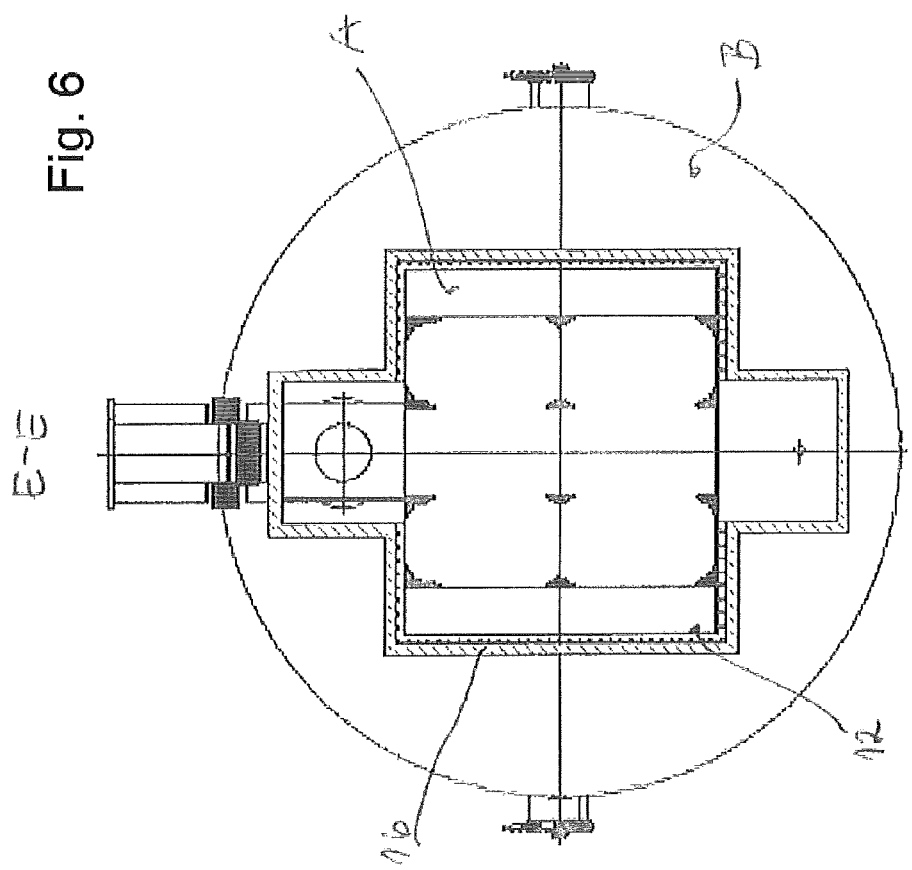

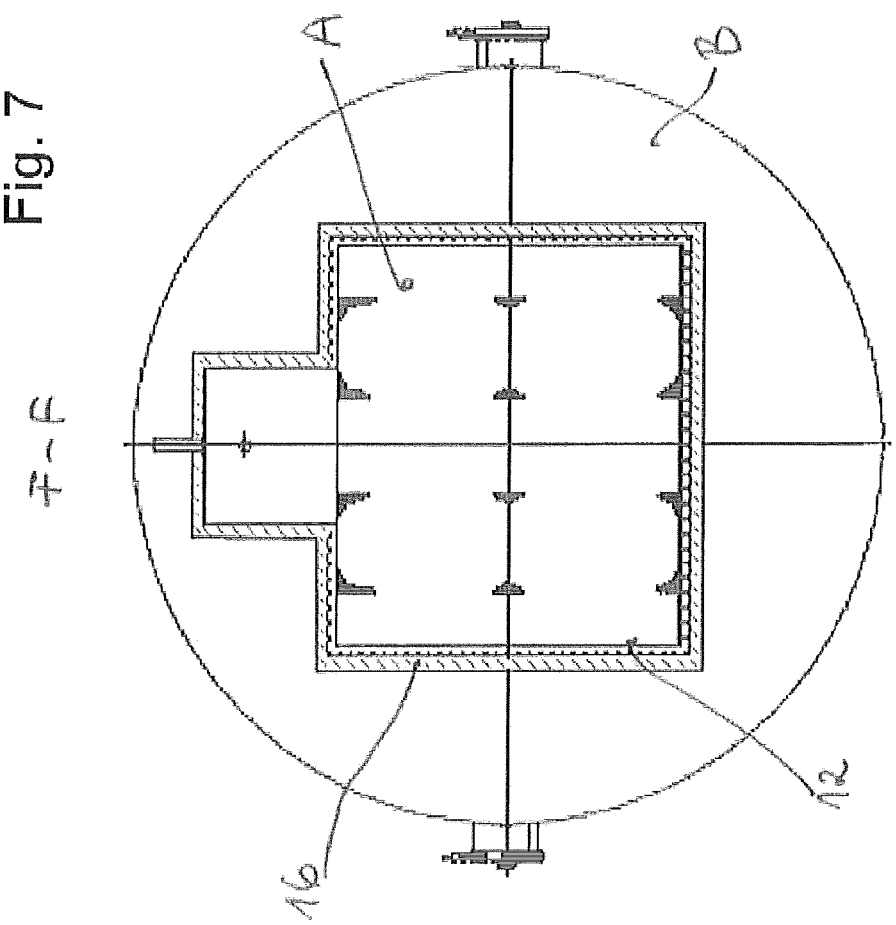

REACTOR FOR CARRYING OUT AN AUTOTHERMAL GAS-PHASE DEHYDROGENATION

CROSS-REFERENCE TO RELATED APPLICATIONS

This application claims benefit (under 35 USC 119(e)) of U.S. Provisional Application 61/514,100, filed Aug. 2, 2011, which is incorporated by reference.

BACKGROUND OF THE INVENTION

The invention relates to a reactor for carrying out autothermal gas-phase dehydrogenations using a heterogeneous catalyst configured as a monolith and also a process using the reactor.

Ceramic or metallic monoliths have become established as catalyst supports for noble metal catalysts in mobile and stationary offgas purification. The channels offer a low resistance to flow and at the same time uniform accessibility to the outer catalyst surface for gaseous reaction media. This is advantageous compared to disordered beds in which a large pressure drop results from numerous deflections in the flow around the particles and the catalyst surface may not be uniformly utilized. The use of monoliths is generally of interest for catalytic processes having high volume flows under adiabatic reaction conditions at high temperatures. In chemical process technology, these features apply particularly to dehydrogenation reactions which occur in the temperature range from 400° C. to 700° C.

Progress in catalyst technology has made selective combustion of the dehydrogenation hydrogen in the presence of hydrocarbons possible, as described, for example, in U.S. Pat. No. 7,034,195. Such a mode of operation is referred to as autothermal dehydrogenation and allows dehydrogenation reactors to be heated directly, so that complicated apparatuses for indirect preheating and intermediate heating of the reaction mixture become unnecessary. One such process is described, for example, in US 2008/0119673. However, this process has the serious disadvantage that the dehydrogenation is carried out over a heterogeneous catalyst in pellet form: the high flow resistance of beds of pellets requires a large reactor cross section and a correspondingly low flow velocity in order to limit the pressure drop in the catalytically active layer. This disadvantage is compensated by a very complicated apparatus for introducing and distributing the oxygen, which impairs the advantage of autothermal dehydrogenation.

The European patent application EP 09 177 649.2, which is not a prior publication, discloses a reactor and also a process for the autothermal gas-phase dehydrogenation of hydrocarbons using heterogeneous catalysts configured as monoliths, which ensure safe control of the combustible reaction media at high reaction temperatures, frequently in the range from about 400 to 700° C., and also easy accessibility and handling of the monoliths, in particular on equipping the reactor and also on changing the catalyst.

EP 09 177 649.2 provides a reactor in the form of an essentially horizontal cylinder for carrying out an autothermal gas-phase dehydrogenation of a hydrocarbon-comprising gas stream by means of an oxygen-comprising gas stream to give a reaction gas mixture over a heterogeneous catalyst configured as monolith, wherein the interior of the reactor is divided by a detachable, cylindrical or prismatic housing G which is arranged in the longitudinal direction of the reactor and is gastight in the circumferential direction and open at two end faces of the housing into an inner region A having one or more catalytically active zones, in which a packing composed of monoliths stacked on top of one another, next to one another and behind one another and before each catalytically active zone in each case a mixing zone having solid internals are provided, and an outer region B arranged coaxially to the inner region A, with one or more feed lines for the hydrocarbon-comprising gas stream to be dehydrogenated into the outer region B, deflection of the hydrocarbon gas stream to be dehydrogenated at one end of the reactor and introduction via a flow equalizer into the inner region A, with one or more feed lines which can be regulated independently of one another, where each feed line supplies one or more distribution chambers for the oxygen-comprising gas stream into each of the mixing zones and with a discharge line for the reaction mixture of the autothermal gas-phase dehydrogenation at the same end of the reactor as the feed line for the hydrocarbon gas stream to be dehydrogenated.

At the end of the reactor at which the discharge line for the reaction gas mixture from the autothermal gas-phase dehydrogenation is arranged, it is advantageous to provide a shell-and-tube heat exchanger having a bundle of tubes through which the reaction gas mixture from the autothermal gas-phase dehydrogenation is passed and also intermediate spaces between the tubes through which the hydrocarbon-comprising gas stream to be dehydrogenated is passed in countercurrent to the reaction mixture from the autothermal gas-phase dehydrogenation.

An improved reactor from a safety point of view is described in EP 10 196 216.5, namely a reactor in the form of an essentially horizontal cylinder or prism for carrying out an autothermal gas-phase dehydrogenation of a hydrocarbon-comprising gas stream by means of an oxygen-comprising gas stream to give a reaction gas mixture over a heterogeneous catalyst configured as monolith, where the interior of the reactor is divided by a detachable, cylindrical or prismatic, gastight housing G which is arranged in the longitudinal direction of the reactor into an inner region A having one or more catalytically active zones, in each of which a packing composed of monoliths stacked on top of one another, next to one another and behind one another and before each catalytically active zone in each case a mixing zone having solid internals are provided, and an outer region B arranged coaxially to the inner region A, and a heat exchanger is provided at one end of the reactor connected to the housing G, with one or more feed lines for the hydrocarbon-comprising gas stream to be dehydrogenated, with one or more feed lines which can be regulated independently of one another, where each feed line supplies one or more distribution chambers, for the oxygen-comprising gas stream into each of the mixing zones and with a discharge line for the reaction gas mixture of the autothermal gas phase dehydrogenation, and where the outer region B is supplied with a gas which is inert under the reaction conditions of the autothermal gas-phase dehydrogenation and the hydrocarbon-comprising gas stream to be dehydrogenated is introduced via a feed line into the heat exchanger, is heated by means of the reaction gas mixture in countercurrent by indirect heat exchange and conveyed further to the end of the reactor opposite the heat exchanger, redirected there, introduced via a flow equalizer into the inner region A and mixed with the oxygen-comprising gas stream in the mixing zones, whereupon the autothermal gas-phase dehydrogenation takes place in the inner region A of the reactor.

Thus, a reactor having an outer reactor wall, i.e. a pressure-bearing shell which is not contacted by a medium, neither by the hydrocarbon-comprising stream nor by the oxygen-comprising stream, is provided.

A SUMMARY OF THE INVENTION

In the light of the above, it was an object of the present invention to improve the above-described reactor further, in particular in respect of the energy consumption.

The object is achieved by a reactor in the form of an essentially horizontal cylinder or prism for carrying out an autothermal gas-phase dehydrogenation of a hydrocarbon-comprising gas stream by means of an oxygen-comprising gas stream to give a reaction gas mixture over a heterogeneous catalyst configured as monolith, where the interior of the reactor is divided by a cylindrical or prismatic gastight housing G which is arranged in the longitudinal direction of the reactor into an inner region A having one or more catalytically active zones, in which a packing composed of monoliths stacked on top of one another, next to one another and behind one another and before each catalytically active zone in each case a mixing zone having solid internals are provided, and an outer region B arranged coaxially to the inner region A, and a heat exchanger is provided at one end of the reactor connected to the housing G, with one or more feed lines for the hydrocarbon-comprising gas stream to be dehydrogenated, with one or more feed lines which can be regulated independently of one another, where each feed line supplies one or more distribution chambers, for the oxygen-comprising gas stream into each of the mixing zones and with a discharge line for the reaction gas mixture of the autothermal gas-phase dehydrogenation, where the outer region B is supplied with a gas which is inert under the reaction conditions of the autothermal gas-phase dehydrogenation and the hydrocarbon-comprising gas stream to be dehydrogenated is introduced via a feed line into the heat exchanger, is heated in the heat exchanger by means of the reaction gas mixture in countercurrent by indirect heat exchange and conveyed further to the end of the reactor opposite the heat exchanger, redirected there, introduced via a flow equalizer into the inner region A and mixed with the oxygen-comprising gas stream in the mixing zones, whereupon the autothermal gas-phase dehydrogenation takes place in the inner region A of the reactor.

wherein the inner region A is insulated from the outer region B of the reactor by means of a microporous high-performance insulation material (16) having a thermal conductivity $\lambda$ at temperatures up to 700° C. of less than 0.05 W/m*K.

It has been found that the heat losses of the reactor described in EP 10 196 216.5 can be significantly reduced by insulating the inner region A of the reactor into which feed streams, i.e. the hydrocarbon-comprising gas stream to be dehydrogenated and the oxygen-comprising gas stream, are fed, mixed with one another and react to give a reaction gas mixture which is preheated by indirect heat exchange with the hydrocarbon-comprising feed gas stream and subsequently leaves the reactor from the outer region B of the reactor using a microporous high-performance insulation material. Since the autothermal gas-phase dehydrogenation takes place in the inner region A of the reactor at high temperatures of from about 400 to 700° C., the thermal insulation of this is of greater importance than in the outer region B.

A BRIEF DESCRIPTION OF THE FIGURES

FIG. 1 shows a longitudinal section in the vertical plane through a preferred embodiment of a reactor according to the invention in the form of an essentially horizontal cylinder, FIG. 2 shows a longitudinal section through a preferred embodiment of a reactor according to the invention in the form of an upright cylinder with vertical longitudinal axis, FIG. 3 shows a longitudinal section through the reactor shown in FIG. 1 in the horizontal plane, FIG. 4 shows a cross section through the reactor shown in FIG. 1 in the plane C C, FIG. 5 shows a cross section through the reactor shown in FIG. 1 in the plane D D, FIG. 6 shows a cross section through the reactor shown in FIG. 1 in the plane E E, FIG. 7 shows a cross section through the reactor shown in FIG. 1 in the plane F F and FIG. 8 schematically shows the thermal conductivity values as a function of the temperature for microporous high-performance insulation materials WDS® from Porextherm compared to conventional insulation materials.

A DETAILED DESCRIPTION OF THE INVENTION

According to the invention, microporous high-performance materials having thermal conductivity values $\lambda$ at temperatures up to 700° C. of <0.05 W/m*K are used for this purpose. Such materials are described as superinsulations having a continuous structure in the VDI-Wärmeatlas, 9th edition 2002, section Kf 8. Superinsulations are accordingly thermal insulations whose total heat transmission is significantly lower than that of static air.

The insulation according to the invention composed of a microporous high-performance insulation material has a significantly lower heat capacity and a significantly smaller volume at the same heat transfer coefficient compared to conventional fiber insulations. However, a low heat capacity is indispensible for controlling the temperature during the burning-off process in the regeneration of the catalyst; the low volume in particular also favors the integration of all thermally stressed components in a single common housing.

As microporous high-performance insulation materials, it is possible to use, in particular, materials composed of siliceous substances. These are, in particular, made up of finely divided silica as main constituent and an opacifier to minimize infrared radiation as further constituent. It is also possible to use a mixture as opacifier. The microporous high-performance insulation materials are, in particular, in the form of microporous particles having an average pore size of about 20 nm.

Such materials are, for example, known as WDS® Ultra from Porextherm: WDS® Ultra comprises about 80% of silicon dioxide as main constituent together with about 15% of silicon carbide and ensures particularly low heat transmission both by thermal conduction, by convection and by thermal radiation:

Owing to the cell structure of the microporous material used and the fact that the particles of material are spherical, the contact points between the particles are infinitely small, resulting in a very low solid-state conductivity.

Heat transfer as a result of gas heat conduction is likewise very low. Owing to the cell structure of the microporous material, with an average pore size of 20 nm which is smaller than the average free path length of the gas molecules, this leads mainly to collisions of the gas molecules with the pore walls, as a result of which energy exchange between the individual molecules is reduced to a minimum.

Heat transfer by thermal radiation takes place by means of electromagnetic waves and becomes increasingly important as the temperature increases, in particular above 400° C. The addition of infrared-absorbing materials (opacifiers) to the microporous material mixture considerably restricts this type of heat transfer, too.

For the above reasons, a very much greater insulating effect can be achieved by means of the microporous insulation materials used according to the invention compared to conventional insulation materials such as mineral fibers, lightweight refractory bricks or inorganic insulation boards. Thus, for example, the layer thickness can be reduced by a factor of 6 and the weight by a factor of from 2 to 15 for the same insulating effect.

A further improvement can be achieved by use of vacuum technology by using evacuated panels or shaped parts made from boards.

In particular, the housing G, the heat exchanger, the feed line for the hydrocarbon-comprising gas stream to be dehydrogenated and the feed lines for the oxygen-comprising gas stream are insulated from the outer region B of the reactor by means of the microporous high-performance insulation material.

The microporous high-performance insulation material is advantageously used in the form of boards or shaped parts produced from boards.

The boards or shaped parts produced from boards are preferably enveloped in a layer of a material which increases the mechanical stability thereof.

Metal, particularly preferably stainless steel or aluminum, can advantageously be used as material for this purpose.

The shaped parts produced from boards of the microporous high-performance insulation material can advantageously be configured so as to be able to be interlocked with one another so as to always ensure continuous insulation under mechanical and thermal stress.

A cylindrical or prismatic housing G is provided in the longitudinal direction of the reactor and divides the interior of the reactor into an inner region A and an outer region B arranged concentrically around the inner region A.

The outer region B is supplied with a gas which is inert under the reaction conditions of the autothermal gas-phase dehydrogenation, i.e. a gas or gas mixture which does not participate directly in the reaction of the autothermal gas-phase dehydrogenation, in particular selected from among water, carbon dioxide, nitrogen and noble gases or mixtures thereof. Steam is preferably used as gas which is inert under the reaction conditions of the autothermal gas-phase dehydrogenation since it can be separated off from the reaction gas mixture again in a simple way, by condensation.

The gas which is inert under the reaction conditions of the autothermal gas-phase dehydrogenation is preferably passed as purge gas stream through the inner region A at a low mass flow compared to the mass flow of the hydrocarbon-comprising gas stream, i.e. a mass flow of from 1/5 to 1/100, preferably a mass flow of from 1/10 to 1/50, based on the mass flow of the hydrocarbon-comprising gas stream, under a low gauge pressure of from 2 to 50 mbar, preferably from 25 to 30 mbar, based on the pressure in the inner region A.

The purge gas stream can advantageously be conveyed through the outer region B by being introduced into the outer region B of the reactor via one or more feed lines at one end of the reactor and being conveyed further into the inner region A of the reactor at the opposite end of the reactor, preferably via one or more connecting line(s) which are advantageously arranged at an angle other than 90° to the feed line for the hydrocarbon-comprising gas stream to be dehydrogenated.

The one or more connecting line(s) which conduct the purge gas stream from the outer region B into the inner region A are preferably configured so that they are backflow-free, for example by means of a helical shape. The inlet from the outer region B into the connecting line for the purge gas stream should preferably be arranged as high as possible in the outer region B of the reactor.

The purge gas stream continually flushes the outer region B of the reactor and keeps it free of components of the reaction gas mixture.

A heat exchanger, which can, in particular, be a shell-and-tube heat exchanger or a plate heat exchanger, is connected at one end of the housing G. in the case of a shell-and-tube heat exchanger, the connection between this and the housing G is configured so that the inner region A communicates with the interior of the tubes of the shell-and-tube heat exchanger. In the case of a plate heat exchanger, the inner region A of the reactor communicates with the gaps between the plates of the plate heat exchanger.

The intermediate space between the tubes of the shell-and-tube heat exchanger or between in each case two metal sheets welded together to form a heat exchange plate of the plate heat exchanger is connected, via a line which leads to the end of the reactor opposite the heat exchanger and is redirected there, to the end of the housing G opposite the heat exchanger and thus to the inner region of the reactor so as to form a gastight seal from the outer region B.

The hydrocarbon-containing stream is conveyed through the intermediate space between the tubes of the shell-and-tube heat exchanger or, in the case of a plate heat exchanger, through the intermediate spaces between the metal sheets which in each case form a heat exchanger plate, heated by the product gas stream circulating in countercurrent through the tubes or through the gaps between the plates of the plate heat exchanger, conveyed to the opposite end of the reactor, redirected there and introduced into the inner region A of the housing.

The autothermal gas-phase dehydrogenation takes place over a heterogeneous catalyst which is present in the form of monoliths.

For the present purposes, a monolith is a one-piece, parallelepipedal block having a plurality of continuous channels which are arranged parallel to one another and have a narrow cross section in the range from about 0.5 to 4 mm.

The monoliths are preferably formed by a ceramic material as support material onto which a catalytically active layer has been applied, preferably by the washcoating process.

The monoliths which are stacked next to one another, above one another and behind one another to form a packing are preferably enclosed in an expandable mat or in a mineral fiber nonwoven and inserted in a casing having a clamping device. As mineral fiber nonwovens, preference is given to using nonwovens as are known for use for offgas catalysts, for example Interam® mats from 3M®.

Expandable mats are known from catalytic offgas purification and are described, for example, in DE-A 40 26 566: they consist essentially of ceramic fibers with embedded mica. As a result of the embedded mica, the expandable mat seeks to expand at increasing temperatures, as a result of which the body enveloped therein is held particularly securely even at elevated temperatures.

The mineral nonwovens or expandable mats are selected so that they expand on heating and seal the generally ceramic monoliths against the housing, in particular prevent rubbing of the monoliths against the housing and bypass flow of the reaction gas mixture along the inner wall of the housing.

The expandable mats in which the monoliths are enclosed ensure a stable position of the monoliths since they generate a clamping force when they undergo thermal expansion. However, the clamping force can decrease in the event of incorrect conditions. It can therefore be advantageous to provide a clamping device: for this purpose, the expandable mats are inserted at their end corresponding to the exit for the reaction gas mixture into a U-profile formed by a high-temperature-resistant woven mesh which can, for example, be metallic. Metal profiles which have a cross section corresponding to the cross section of the expandable mats and are attached to the mats and increase in width in the flow direction of the reaction gas mixture are arranged in the extension of the expandable mats. As a result, the metal profiles act as supports to prevent shifting of the expandable mats in the flow direction of the reaction gas mixture.

The monoliths enclosed in expandable mats are arranged in a housing.

The housing is advantageously made of a material which is mechanically and chemically stable at the high reaction temperature, frequently in the range from about 400 to 700° C., and also has no catalytic activity for the autothermal gas-phase dehydrogenation.

The housing is preferably made of a material which is heat-resistant, in particular a stainless steel having the material number 1.4541, 1.4910 or 1.4841.

The housing should be very thin in order to give a very low heat capacity and thus limit the heat losses between the outer region B and the inner region A.

The housing can preferably be thermally insulated.

The housing can preferably be installed unfastened in the reactor.

The housing is preferably configured as a cuboid.

The side walls of the housing configured as a cuboid are preferably configured so as to be removed individually so that a complete packing or individual monoliths of a packing in a catalytically active zone can be replaced.

The individual monoliths are stacked beside one another, above one another and behind one another in the required number in order to fill out a catalytically active zone and form a packing.

At least one mixing zone having fixed internals which are not catalytically active is provided before each packing. Mixing of the hydrocarbon-comprising gas stream with the oxygen-comprising stream occurs in the mixing zone, with mixing of the oxygen-comprising gas stream with the hydrocarbon-comprising feed stream occurring in the first mixing zone in the flow direction and intermediate introduction of an oxygen-comprising gas stream into the hydrocarbon-comprising reaction mixture yet to be dehydrogenated being carried out in each of the subsequent (in the flow direction) mixing zones.

The hydrocarbon-comprising gas stream to be dehydrogenated can preferably be introduced into the heat exchanger at two or more places, in particular as a main stream having a higher mass flow and one or more secondary streams having a lower mass flow compared to the main stream.

To heat the hydrocarbon-comprising gas stream to be dehydrogenated, one or more supplementary heating devices can be provided in addition to the heat exchanger. As supplementary heating, preference is given to introducing hydrogen through the feed line for the hydrocarbon-comprising gas stream to be dehydrogenated as close as possible to the inlet into the mixing zones arranged upstream of each catalytically active zone.

As an alternative or in addition, the supplementary heating can be provided as electric heating which is installed, preferably detachably, as plug-in system, within the outer region B of the reactor in the feed line for the hydrocarbon-comprising gas stream after the latter has exited from the heat exchanger. As an alternative or in addition, a muffle burner can be provided as supplementary heating.

As a result of the reactor being preferably designed as an essentially horizontal cylinder, the inner space A which comprises the monolith packings is supported over a large area and thus subjected to decreased mechanical stress. Furthermore, this reactor design makes accessibility to the individual monolith packings easier.

The outer wall of the reactor is preferably made of an alloy steel approved for pressure vessels, in particular a black steel, preferably Kesselblech HII, or an alloy steel having the material number 1.4541 or 1.4910. The outer wall of the reactor can also be covered with a chamotte lining.

Each mixing zone preferably comprises a tube distributor formed by a plurality of parallel plug-in tubes which are arranged in a plane perpendicular to the longitudinal direction of the reactor and are connected with one or more of the distributor chambers and have a plurality of uniformly spaced outlet openings for exit of the oxygen-comprising gas stream from the plug-in tube, and also a plurality of uniformly spaced mixing elements.

The mixing elements can advantageously be configured as mixing plates.

The heat exchanger is preferably a shell-and-tube heat exchanger.

The shell-and-tube heat exchanger is advantageously made of a highly heat-resistant stainless steel, in particular a stainless steel having the material number 1.4541 or 1.4910. The tubes of the shell-and-tube heat exchanger are advantageously installed at both ends in tube plates without leaving a gap by backplate welding and the tube plates of the shell-and-tube heat exchanger are clad on the hot gas side of the plates with a heat-resistant stainless steel, in particular a stainless steel having the material number 1.4841.

A flow straightener is preferably arranged at the end face of the housing G at which the hydrocarbon-comprising gas stream is introduced into the inner region A.

The invention also provides a process for carrying out autothermal dehydrogenations using the above-described reactors.

In a preferred, fully continuous mode of operation, two or more reactors can be used, with at least one reactor being utilized for the autothermal gas-phase dehydrogenation and at the same time at least one further reactor being regenerated.

The autothermal gas-phase dehydrogenation is preferably an autothermal dehydrogenation of propane, butane, i-butane or butene.

The reactor of the invention and the process of the invention have, in particular, the advantage that the energy balance of the autothermal gas-phase dehydrogenation is significantly improved compared to conventional reactors by use of a superinsulator composed of a microporous high-performance insulation material.

The invention is illustrated below with the aid of an example and a drawing.

In the drawing:

FIG. 1 shows a longitudinal section in the vertical plane through a preferred embodiment of a reactor according to the invention in the form of an essentially horizontal cylinder, FIG. 2 shows a longitudinal section through a preferred embodiment of a reactor according to the invention in the form of an upright cylinder with vertical longitudinal axis, FIG. 3 shows a longitudinal section through the reactor shown in FIG. 1 in the horizontal plane, FIG. 4 shows a cross section through the reactor shown in FIG. 1 in the plane C-C, FIG. 5 shows a cross section through the reactor shown in FIG. 1 in the plane D-D, FIG. 6 shows a cross section through the reactor shown in FIG. 1 in the plane E-E, FIG. 7 shows a cross section through the reactor shown in FIG. 1 in the plane F-F and FIG. 8 schematically shows the thermal conductivity values as a function of the temperature for microporous high-performance insulation materials WDS® from Porextherm compared to conventional insulation materials.

Identical reference numerals in the figures in each case denote identical or corresponding features.

The longitudinal section in the vertical plane in FIG. 1 schematically shows a preferred embodiment of a reactor 1 according to the invention which is supplied with a hydrocarbon-comprising gas stream 2 to be dehydrogenated via a feed line 7 and with an oxygen-comprising gas stream 3 via feed lines 9 with distributor chambers 10.

FIG. 1 shows that the housing G divides the interior of the reactor 1 into an inner region A and an outer region B.

FIG. 1 shows that the housing G divides the interior of the reactor 1 into an inner region A and an outer region B. In the inner region A, there are, for example, three catalytically active zones 5 in each of which a packing made up of monoliths 4 which are not shown in detail and are stacked on top of one another, next to one another and behind one another and a mixing zone 6 having solid internals is provided before each catalytically active zone 5. The hydrocarbon-comprising gas stream 2 to be dehydrogenated is passed through a heat exchanger 12, heated by indirect heat exchange with the reaction gas mixture and conveyed further to the opposite end of the reactor, diverted there, introduced via a flow equalizer 8 into the inner region A, mixed in the mixing zones 6 with the oxygen-comprising gas stream 3, whereupon the autothermal gas-phase dehydrogenation takes place in the catalytically active zones 5 provided with monoliths 4. The reaction gas mixture is taken off from the reactor via a collection box 13 at the outlet of the heat exchanger 12 and through the discharge line 11.

The reference numeral 14 denotes the transition from a conical geometry to a cuboidal geometry at the entrance to the inner region A and the reference numeral 15 denotes the transition from cuboidal to conical at the product gas outlet from the heat exchanger 12.

The reference numeral 16 denotes the microporous high-performance insulation material which is shown as a hatched region and insulates the inner region A of the reactor 1 from the outer region B.

Figure 1:
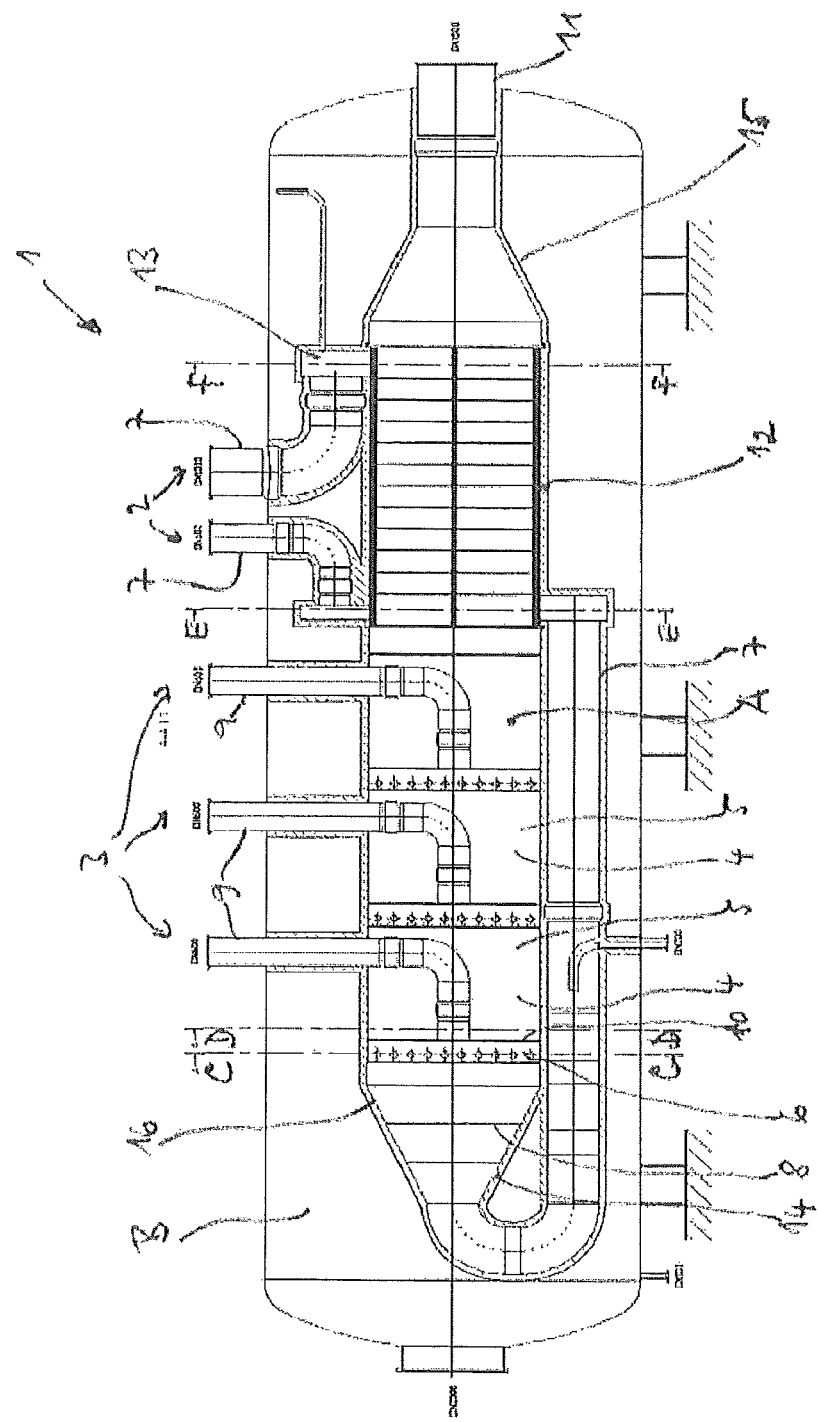
Figure 2:
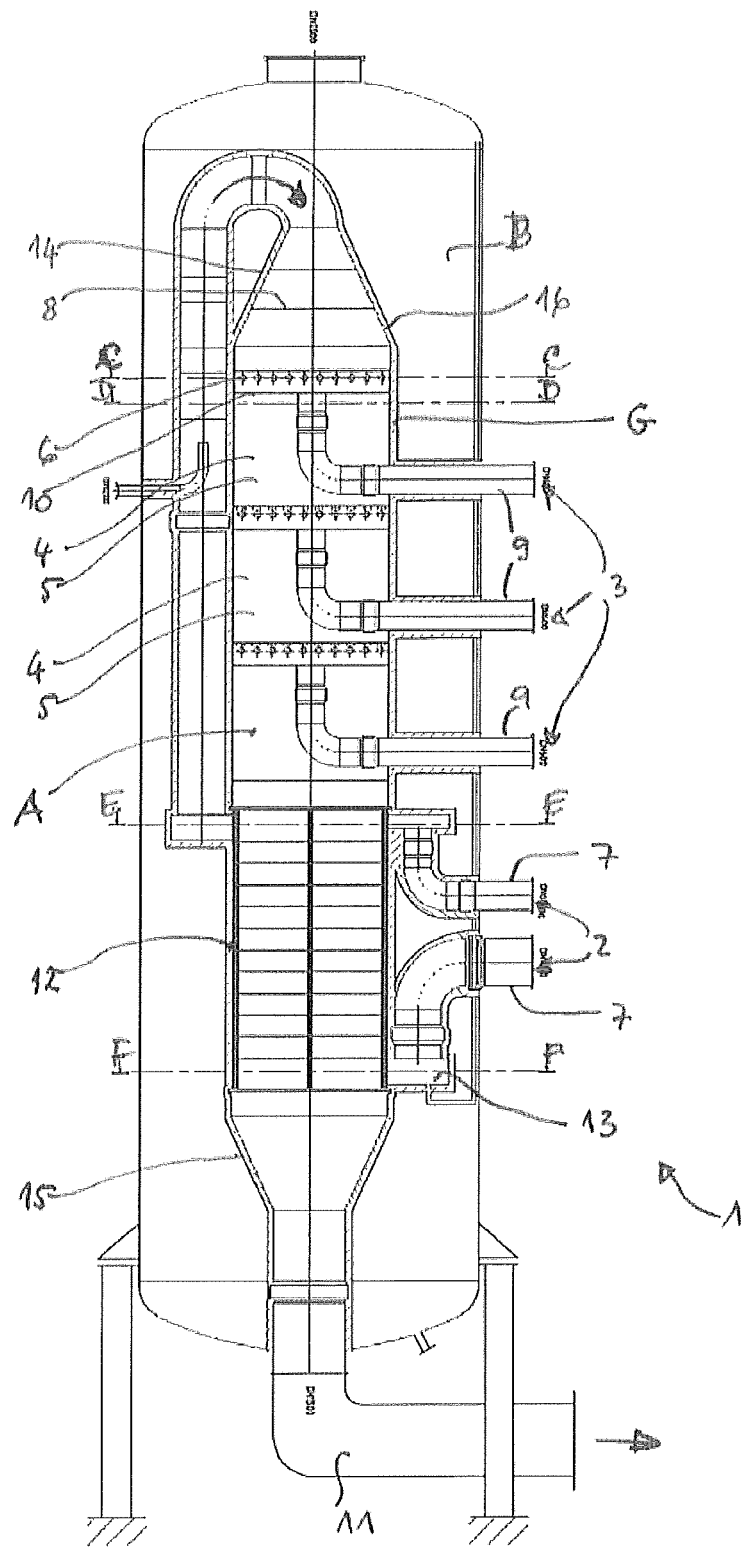
FIG. 2 shows a reactor analogous to that shown in FIG. 1 which, however, is upright with a vertical longitudinal axis.
Figure 3:
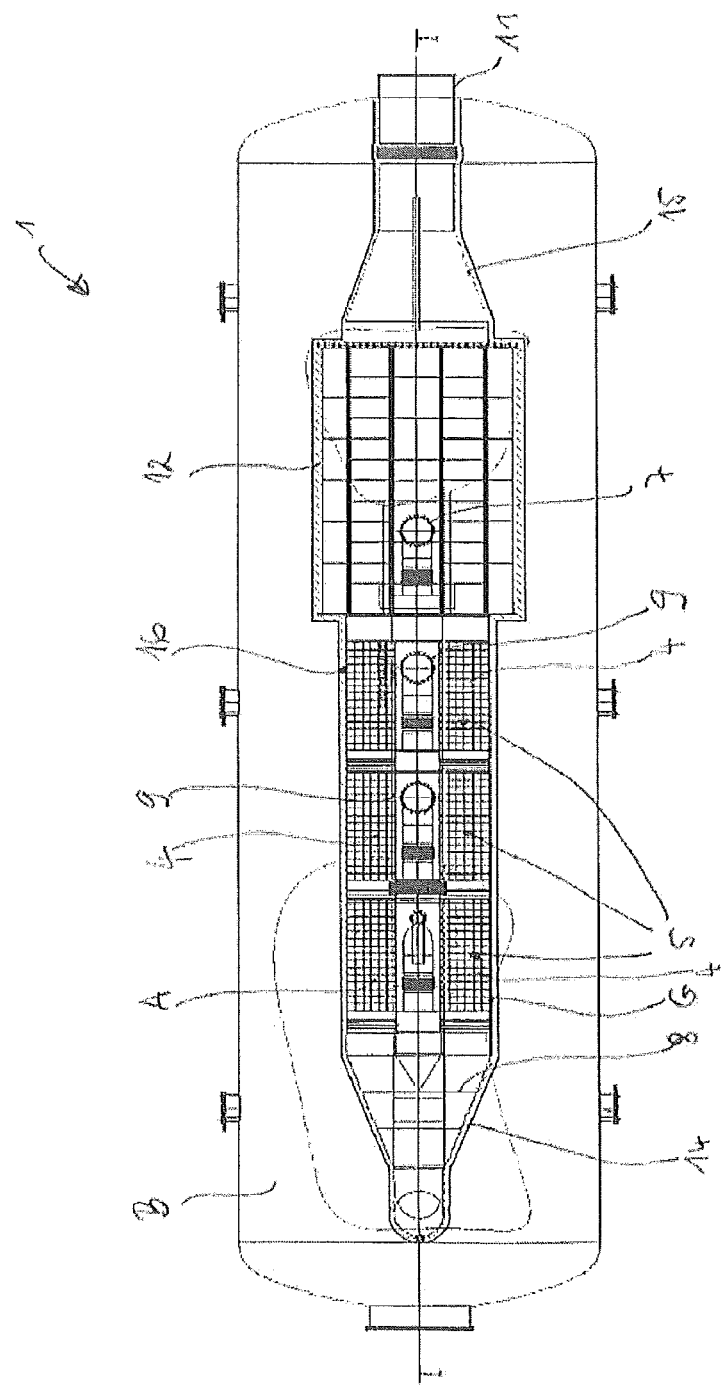
FIG. 3 shows the same reactor as shown in FIG. 1 but as longitudinal section in the horizontal plane.

FIG. 4 shows a cross section through the reactor shown in FIGS. 1 and 2 in the region of the mixing zone 6 (section C-C), FIG. 5 shows a cross section through the same reactor in the region of the catalytically active zone 5 (section D-D), FIG. 6 shows a cross section through the same reactor in the region of the reaction gas inlet into the heat exchanger 12, FIG. 7 shows a cross section through the same reactor in the region of the reaction gas outlet from the heat exchanger 12.

In all cross-sectional views (FIGS. 4 to 7), the insulation composed of the microporous high-performance insulation material (reference numeral 16) which insulates the inner region A from the outer region B can be seen.

Figure 8:
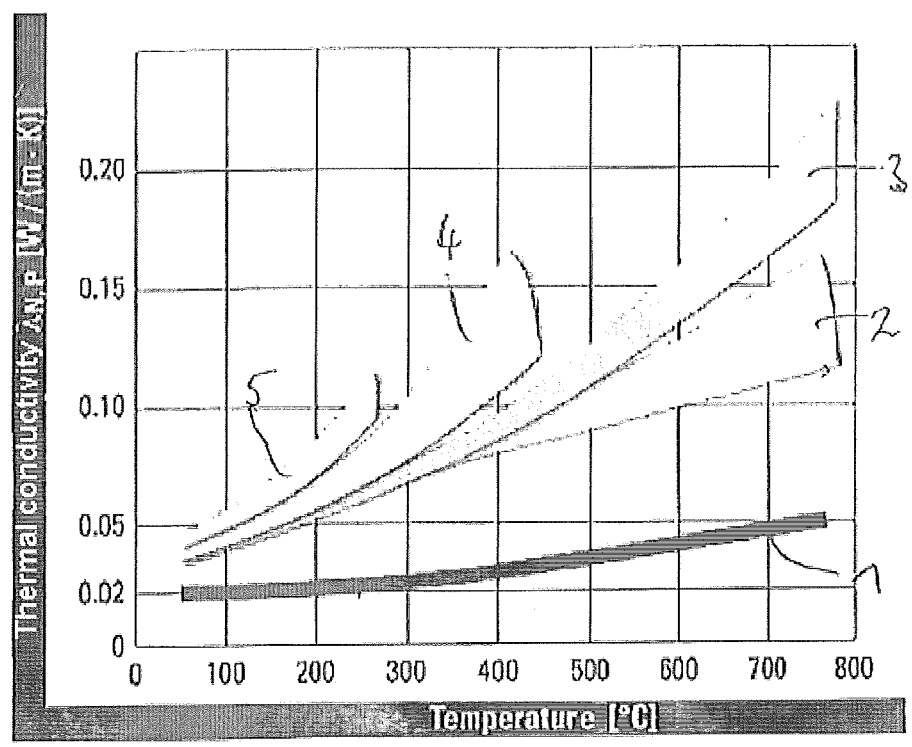

FIG. 8 illustrates the extremely low thermal conductivity values for the microporous high-performance insulation materials, e.g. WDS® from Porextherm, curve 1, used according to the invention compared to conventional insulation materials, i.e. curve 2 for silicon-silicate boards, curve 3 for calcium-magnesium silicate fiber mats, curve 4 for glass wool (boards and mats) and for rock wool (mats), with the thermal conductivities $\lambda$ in W/m*K being plotted on the ordinate against the temperature in ° C. on the abscissa.

The invention will be illustrated below with the aid of an example. A preferred embodiment of a reactor 1 on an industrial scale will be described in detail by way of example:

EXAMPLE

The dimensions of the outer shell (essentially horizontal cylinder with convex plate ends) are:
length: 24 500 mm,
diameter: 6000 mm,
material of the outer shell: HII
design data for the outer shell:
pressure: 7 bara
temperature: 350° C.

The reactor comprises the following individual components (material 1.4541):
1 off feed line for feed gas DN1000 (reference numeral 7 in FIG. 1) (main stream 80-100% regulatable) through outer reactor wall to the integrated heat exchanger (reference numeral 12 in FIG. 1).
1 off integrated heat exchanger having a shell-and-tube construction, reference numeral 12;
  feed gas flows in cross-countercurrent on the shell side; product gas flows through 11 000 tubes 20 mm×2 mm×6000 mm; triangular positioning 26 mm; tubes are distributed over two rectangular regions having respective dimensions of 3370 mm×1000 mm.
  The welding of the tubes onto the tube plates is effected behind the plates. The heat exchanger has a floating head compensator on the cold side.
1 off feed line for feed gas DN600 (bypass flow 0-20% regulatable) through the outer reactor wall to the integrated heat exchanger.
1 off connecting line for feed gas DN1000 from the outlet of the integrated heat exchanger 12 to the reactor inlet. Electric supplementary heating is installed in the connecting line.
1 off feed line DN200 and mixing-in device for heating gas 17 into the connecting line between heat exchanger 12 and entrance into the inner region A; mixing-in device configured as perforated tube system. Hydrogen is used as heating gas.

1 off transition 14 conical from DN1000 round to cuboidal (entry into the housing G) 3370 mm×2850 mm with 3 integrated perforated plates as flow equalizers 8.

3 off mixing zones 6 with fixed internals channels before each catalytically active zone 5, comprising in each case 20 distributor tubes DN125.

1 off housing G for accommodation of the monoliths 4 dimensions: 3370 mm×2850 mm×8500 mm The monoliths are preassembled to form larger packs for the purpose of easier installation. One pack comprises 6×4 monoliths which are separated by expanded mats. The mats are protected against disintegration and abrasion at the end face in the flow direction by means of an adhesively bonded metal screen. The individual monoliths 4 are secured against movement by spacers.

Each packing module is clamped on the outside by means of a robust box. The individual packing modules are configured as push-in modules. Sealing of the push-in modules against the actual reactor housing is effected by means of a thin sealing mat.

3 off catalytically active zones 5 which are appropriately equipped with the packing modules of monoliths 4.

Each catalytically active zone 5 comprises 15 monolith rows arranged behind one another. Each monolith row comprises 240 monoliths. Overall, a catalytically active zone 5 comprises 3600 monoliths having the dimensions 150 mm×150 mm×150 mm.

The individual monolith rows are spaced. Appropriate temperature measuring devices for regulating and controlling the process are installed in these spaces.

1 off transition from housing G to integrated heat exchanger 12 dimensions: 3370 mm×2850 mm×700 mm; rectangular The transition is configured as a welded construction.

1 off transition 15 for the reaction gas mixture from the integrated heat exchanger 12 from rectangular 3370 mm×2850 mm to round DN1500; configuration of the transition conical.

1 off outlet line 11 DN1500 for the reaction gas mixture through the outer reactor wall.

3 off feed lines DN600 9 for O₂-comprising gas through the outer reactor wall to the distributor chamber 10 of the respective catalytically active zone 5.

All internals are provided with a microporous high-performance insulation material (superinsulation) 16, e.g. composed of WDS® from Porextherm, to insulate the inner region A from the outer region B. This superinsulation is protected against abrasion and moisture by means of a metal casing (encapsulation). The pressure-bearing outer wall of the reactor is insulated on the outside.

The invention claimed is:

1. A reactor in the form of a cylinder or prism for carrying out an autothermal gas-phase dehydrogenation of a hydrocarbon-comprising gas stream by means of an oxygen-comprising gas stream to give a reaction gas mixture over a heterogeneous catalyst configured as monolith, where the interior of the reactor is divided by a cylindrical or prismatic gastight housing G which is arranged in the longitudinal direction of the reactor into an inner region A having one or more catalytically active zones, in which a packing composed of monoliths stacked on top of one another, next to one another and behind one another and before each catalytically active zone in each case a mixing zone having solid internals are provided, and an outer region B arranged coaxially to the inner region A, and a heat exchanger is provided at one end of the reactor connected to the housing G, with one or more feed lines for the hydrocarbon-comprising gas stream to be dehydrogenated, with one or more feed lines which can be regulated independently of one another, where each feed line supplies one or more distribution chambers, for the oxygen-comprising gas stream into each of the mixing zones and with a discharge line for the reaction gas mixture of the autothermal gas-phase dehydrogenation, where the outer region B is supplied with a gas which is inert under the reaction conditions of the autothermal gas-phase dehydrogenation and the hydrocarbon-comprising gas stream to be dehydrogenated is introduced via a feed line into the heat exchanger, is heated in the heat exchanger by means of the reaction gas mixture in countercurrent by indirect heat exchange and conveyed further to the end of the reactor opposite the heat exchanger, redirected there, introduced via a flow equalizer into the inner region A and mixed with the oxygen-comprising gas stream in the mixing zones, whereupon the autothermal gas-phase dehydrogenation takes place in the inner region A of the reactor, wherein the inner region A is insulated from the outer region B of the reactor by means of a microporous high-performance insulation material having a thermal conductivity $\lambda$ at temperatures up to 700° C. of less than 0.05 W/m*K.

2. The reactor according to claim 1, which is configured in the form of an essentially horizontal cylinder or prism.

3. The reactor according to claim 1, wherein the housing G, the heat exchanger, the feed line for the hydrocarbon-comprising gas stream to be dehydrogenated and the feed lines for the oxygen-comprising gas stream are insulated from the outer region B of the reactor by means of the microporous high-performance insulation material.

4. The reactor according to claim 3, wherein the microporous high-performance insulation material has been applied to the side facing the outer region B of the reactor of the housing G, the heat exchanger, the feed line for the hydrocarbon-comprising gas stream to be dehydrogenated and the feed line for the oxygen-comprising gas stream.

5. The reactor according to claim 1, wherein a material comprising finely divided silica as main constituent and an opacifier to minimize infrared radiation as further constituent in the form of microporous particles having an average pore size of about 20 nm is used as microporous high-performance insulation material.

6. The reactor according to claim 1, wherein the microporous high-performance insulation material is used in the form of boards or shaped parts produced from boards.

7. The reactor according to claim 6, wherein the boards or the shaped parts produced from boards are enveloped in a layer of a material which increases the mechanical stability thereof.

8. The reactor according to claim 7, wherein the material of which the layer is made is a metal.

9. The reactor according to claim 7, wherein the material of which the layer is made is of stainless steel or aluminum.

10. The reactor according to claim 6, wherein the shaped parts of the microporous high-performance insulation material produced from boards are configured so as to be able to interlock with one another so that they always ensure continuous insulation under mechanical and thermal stress.

11. A process for carrying out an autothermal gas-phase dehydrogenation using the reactor according to claim 1.

12. The process according to claim 11, wherein the autothermal gas-phase dehydrogenation is a dehydrogenation of propane, of butane, of isobutane, of butene or of ethylbenzene.

* * * * *